(12) United States Patent
Wilson et al.

(10) Patent No.: US 7,992,573 B2
(45) Date of Patent: *Aug. 9, 2011

(54) OPTICALLY GUIDED SYSTEM FOR PRECISE PLACEMENT OF A MEDICAL CATHETER IN A PATIENT

(75) Inventors: David F. Wilson, Philadelphia, PA (US);
Gregory J. Schears, Rochester, MN (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1266 days.

This patent is subject to a terminal disclaimer.

(21) Appl. No.: 11/242,688

(22) Filed: Oct. 4, 2005

(65) Prior Publication Data

US 2006/0036164 A1    Feb. 16, 2006

Related U.S. Application Data

(63) Continuation-in-part of application No. 10/482,190, filed on Nov. 2, 2004, now Pat. No. 7,273,056.

(60) Provisional application No. 60/625,002, filed on Nov. 4, 2004.

(51) Int. Cl.
    *A61B 5/00*     (2006.01)
    *A61B 1/00*     (2006.01)

(52) U.S. Cl. ........ 128/899; 600/407; 600/424; 600/473; 600/476

(58) Field of Classification Search ........... 128/897–899
See application file for complete search history.

(56) References Cited

U.S. PATENT DOCUMENTS

| | | | |
|---|---|---|---|
| 4,096,862 A | 6/1978 | DeLuca | 128/348 |
| 4,444,185 A | 4/1984 | Shugar | 128/305 |
| 4,567,882 A | 2/1986 | Heller | 128/11 |
| 4,772,093 A | 9/1988 | Abele et al. | 350/96.25 |
| 4,782,819 A | 11/1988 | Adair | 128/6 |
| 4,875,897 A | 10/1989 | Lee | 604/283 |
| 4,898,175 A | 2/1990 | Noguchi | 128/634 |
| 4,900,933 A * | 2/1990 | Nestor et al. | 250/458.1 |
| 4,945,895 A | 8/1990 | Takai et al. | 128/6 |
| 5,005,180 A | 4/1991 | Edelman et al. | 372/57 |
| 5,005,573 A | 4/1991 | Buchanan | 128/207 |

(Continued)

FOREIGN PATENT DOCUMENTS

WO    WO 02/103409 A2    12/2002

OTHER PUBLICATIONS

PCT International Search Report dated Oct. 7, 2008.

(Continued)

*Primary Examiner* — Charles A Marmor, II
*Assistant Examiner* — Catherine E. Burk
(74) *Attorney, Agent, or Firm* — McCarter & English, LLP

(57) ABSTRACT

A system is provided comprising an optically-guided catheter having a proximal end, a distal end, and at least one lumen. A light-emitting means is coupled to the catheter, the catheter is inserted into place in the patient, and light is emitted as a point or points from a selected location, usually the distal tip, of the catheter to which it is coupled. The system further comprises an external detection device that detects the transdermally projected light, emitted by the light-emitting point from within the patient, thereby indicating precise placement of the catheter within the patient.

14 Claims, 4 Drawing Sheets

U.S. PATENT DOCUMENTS

| | | | |
|---|---|---|---|
| 5,005,592 A | 4/1991 | Cartmell | |
| 5,007,408 A | 4/1991 | Ieoka | 128/6 |
| 5,019,040 A | 5/1991 | Itaoka et al. | 604/95 |
| 5,125,404 A | 6/1992 | Kittrell et al. | 128/634 |
| 5,131,380 A | 7/1992 | Heller et al. | 128/6 |
| 5,196,004 A | 3/1993 | Sinofsky | 606/3 |
| 5,197,470 A | 3/1993 | Helfer et al. | 128/634 |
| 5,263,928 A | 11/1993 | Trauthen et al. | 604/53 |
| 5,268,570 A | 12/1993 | Kim | 250/214 |
| 5,290,275 A | 3/1994 | Kittrell et al. | 606/15 |
| 5,370,640 A | 12/1994 | Kolff | 606/2 |
| 5,415,654 A | 5/1995 | Daikuzono | 606/15 |
| 5,423,311 A | 6/1995 | Snoke et al. | 128/6 |
| 5,423,321 A * | 6/1995 | Fontenot | 600/476 |
| 5,448,582 A | 9/1995 | Lawandy | 372/42 |
| 5,453,086 A | 9/1995 | Weber | 604/20 |
| 5,456,680 A | 10/1995 | Taylor et al. | 606/2 |
| 5,496,305 A | 3/1996 | Kittrell et al. | 606/15 |
| 5,514,128 A * | 5/1996 | Hillsman et al. | 606/7 |
| 5,517,997 A * | 5/1996 | Fontenot | 600/473 |
| 5,540,691 A * | 7/1996 | Elstrom et al. | 606/64 |
| 5,643,251 A | 7/1997 | Hillsman et al. | 606/7 |
| 5,665,052 A | 9/1997 | Bullard | 600/194 |
| 5,728,092 A | 3/1998 | Doiron et al. | 606/15 |
| 5,733,277 A | 3/1998 | Pallarito | 606/7 |
| 5,879,306 A | 3/1999 | Fontenot et al. | 600/473 |
| 5,906,579 A | 5/1999 | Vander Salm et al. | 600/424 |
| 5,947,958 A | 9/1999 | Woodard et al. | 606/15 |
| 5,995,208 A | 11/1999 | Sarge et al. | 356/39 |
| 6,048,349 A | 4/2000 | Winston et al. | 606/108 |
| 6,061,587 A | 5/2000 | Kucharczyk et al. | 600/411 |
| 6,063,093 A | 5/2000 | Winston et al. | 606/108 |
| 6,081,741 A | 6/2000 | Hollis | 600/424 |
| 6,113,588 A | 9/2000 | Duhaylongsod et al. | 606/15 |
| 6,134,003 A | 10/2000 | Tearney et al. | 356/345 |
| 6,146,409 A | 11/2000 | Overholt et al. | 607/88 |
| 6,159,203 A | 12/2000 | Sinofsky | 606/7 |
| 6,178,340 B1 | 1/2001 | Svetliza | |
| 6,230,046 B1 | 5/2001 | Crane et al. | 600/476 |
| 6,236,879 B1 | 5/2001 | Konings | 600/424 |
| 6,246,901 B1 | 6/2001 | Benaron | 600/431 |
| 6,332,089 B1 | 12/2001 | Acker et al. | |
| 6,363,940 B1 * | 4/2002 | Krag | 128/899 |
| 6,366,726 B1 | 4/2002 | Wach et al. | 385/115 |
| 6,445,943 B1 | 9/2002 | Ferre et al. | 600/424 |
| 6,463,313 B1 | 10/2002 | Winston et al. | 600/407 |
| 6,475,226 B1 | 11/2002 | Belef et al. | 606/185 |
| 6,519,485 B2 | 2/2003 | Wiesmann et al. | 600/328 |
| 6,572,609 B1 | 6/2003 | Farr et al. | |
| 6,685,666 B1 | 2/2004 | Fontenot | 604/27 |
| 6,852,109 B2 | 2/2005 | Winston et al. | 606/41 |
| 6,887,229 B1 | 5/2005 | Kurth | 604/525 |
| 6,902,545 B2 | 6/2005 | Bertolero et al. | 604/102.03 |
| 2002/0038120 A1 | 3/2002 | Duhaylongsod et al. | 606/15 |
| 2002/0052597 A1 | 5/2002 | Duhaylongsod et al. | 606/15 |
| 2002/0068866 A1 * | 6/2002 | Zikorus et al. | 600/424 |
| 2002/0108610 A1 | 8/2002 | Christopher | |
| 2002/0115922 A1 * | 8/2002 | Waner et al. | 600/407 |
| 2002/0123696 A1 | 9/2002 | Kokate et al. | 600/549 |
| 2002/0161290 A1 | 10/2002 | Chance | 600/323 |
| 2003/0092995 A1 | 5/2003 | Thompson | 600/473 |
| 2003/0130575 A1 | 7/2003 | Desai | 600/417 |
| 2003/0187360 A1 | 10/2003 | Waner et al. | 600/478 |
| 2003/0191379 A1 | 10/2003 | Benaron et al. | 600/323 |
| 2003/0191398 A1 | 10/2003 | Motz et al. | 600/478 |
| 2004/0019280 A1 | 1/2004 | Waner et al. | 600/466 |
| 2004/0064021 A1 | 4/2004 | Pfeiffer | 600/341 |
| 2004/0064022 A1 | 4/2004 | Korn | 600/342 |
| 2004/0068178 A1 | 4/2004 | Govari | |
| 2004/0073120 A1 | 4/2004 | Motz et al. | 600/478 |
| 2004/0093044 A1 | 5/2004 | Rychnovsky et al. | 607/88 |
| 2004/0236231 A1 | 11/2004 | Knighton et al. | 600/476 |
| 2005/0165462 A1 | 7/2005 | Bays et al. | 607/88 |
| 2005/0240147 A1 | 10/2005 | Makower et al. | 604/96.01 |
| 2006/0041199 A1 | 2/2006 | Elmaleh et al. | |
| 2006/0227316 A1 | 10/2006 | Gatt | |
| 2007/0073160 A1 * | 3/2007 | Imam | 600/476 |
| 2008/0177174 A1 * | 7/2008 | Crane | 600/424 |

OTHER PUBLICATIONS

Addas, et al. *Light-guided Tracheal Puncture for Percutaneous Tracheostomy.* Canadian Journal of Anesthesia 47:919-922 (2000).

Heller et al. *Early Experience with Illuminated Endotracheal Tubes in Premature and Term Infants.* The American Academy of Pediatrics, vol. 75, Issue 4, pp. 664-666. Apr. 1, 1985.

PCT International Search Report dated May 9, 2006.

The Laerdal Foundation. *Trachlight® Stylet and Tracheal Lightwand*; www.laerdal.com.au/document.asp?subnodeid-8619239. Jun. 4, 2005.

University of Virginia Health System. *Airway Management—How to Intubate.* www.healthsystems.virginia.edu/Internet/Anesthesiology-Elective/airway/Intubation.cfm. Jun. 4, 2005.

Weiss, Markus. *Video-Assisted Airway Management.* The Internet Journal of Anesthesiology. 1999. vol. 3, No. 1.

Zanardo V. et al. *Correct Placement of Endotracheal Tube by Single Strand Fiberoptic Light in Prematures. (Initial Clinical Experience).* Padiatr Padol. 1991:26(5):227-8.

Extended European Search Report dated May 21, 2010.

\* cited by examiner

OPTICALLY GUIDED SYSTEM FOR PRECISE PLACEMENT OF A MEDICAL CATHETER IN A PATIENT

CROSS-REFERENCE TO RELATED APPLICATIONS

The present application is a Continuation-in-Part application of U.S. patent application Ser. No. 10/482,190, filed Nov. 2, 2004, as a National Phase application of PCT/US02/19314, filed Jun. 19, 2002, which further claims priority to U.S. Provisional Patent Application No. 60/299,299, filed Jun. 19, 2001. Priority is also claimed to U.S. Provisional Patent Application No. 60/625,002, filed Nov. 4, 2004. The aforementioned patent applications are herein incorporated by reference.

FIELD OF THE INVENTION

The invention relates to the field of optical guidance to accurately place a medical catheter device within a human or animal body, and in particular to optically-guided system, apparatus and methods used to precisely place inserted medical catheters and devices into the vascular system, organs or other anatomical cavities or regions of a patient.

BACKGROUND OF THE INVENTION

Development of permanent implantable catheter systems, temporary diagnostic and therapeutic catheters and implantable devices has resulted in life-saving benefits, and has greatly improved the quality of life of patients across virtually the entire spectrum of medical treatment. However, the proper placement and positioning of invasive catheters, tubes and devices is critical to their effective use. For example, it is typically desirable to apply medications, nutrients or diagnostic probes to a specific location in the body using catheters or tubes.

Positioning of these medical devices is usually done without benefit of any type of real-time visual guidance. Often catheters and catheter-type devices must be steered through a tortuous path and positioned at a site some distance from the proximal insertion point in the patient. The location of the distal tip of this medical device is unknown until some confirmatory study is performed, such as an x-ray. In cases where positioning is particularly critical, x-rays can be used to locate and position the inserted implant, medical device, catheter or tube. Often, following the confirmatory study, the position of the medical device has to be adjusted or may need to be reinserted to achieve proper position of the tip or other critical location(s) on the device.

For example, when an endotracheal tube is used to provide a patient with a mixture of oxygen and air, it is essential that the tube be correctly placed. If the endotracheal tube is in an incorrect position, possibly either too high or too low, either one lung will not be ventilated at all or if the tube is above the vocal cords, neither lung will be ventilated. Radiographs are commonly taken, sometimes at frequent intervals, to establish that an endotracheal tube has been and remains properly located. Similarly, when an orogastric tube is placed into a patient, radiographs are routinely taken to ascertain that the tube ends in the patient's stomach, and not in the duodenum or the esophagus. The same principles apply to the placement of arterial or venous catheters, wherein placement is critical with regard to established reference points.

Some medical devices are subject to movement after insertion due to changes in patient position, weakening of the device's securement to the body, rapid infusion of fluids, or removal of guidewires or introducers used during the device insertion process. This necessitates regular, often at least daily, surveillance of the medical device position with x-rays.

Positioning techniques using x-rays have several shortcomings. Often multiple x-rays are required to locate or confirm the position of an inserted device, subjecting the patient to undesirable levels of ionizing radiation. This problem increases when handling or movement of the patient necessitates periodic rechecking of tube placement. Additionally, x-ray equipment can be large and cumbersome to use, and often is not readily available at the patient bedside when a catheter must be inserted, or placement of an indwelling catheter verified or readjusted. As a result, considerable time and effort are involved in taking repeat radiographs, adding significantly to patient care costs and to delays in optimal therapy. Alternative attempts to properly place the device without the aid of any real-time visual placement tool can make proper positioning of the device a difficult and time-consuming task.

U.S. Pat. No. 4,567,882 (Heller et al.) provides a method for locating the tip of an endotracheal tube inserted into a patient's trachea to provide an airway, wherein the endotracheal tube that is inserted through the patient's mouth or nose includes a means for emitting and laterally projecting a beam of high-intensity visible light (wavelength 4000 to 7700 Å) from a point on the wall of the tube immediately adjacent to the distal end. Consequently, position of the tip of the endotracheal tube can be externally and visually observed as a high intensity visual light, projected laterally through the body to the outside of the patient. However, the heat generated by such a high intensity light over time can cause burns to the delicate tissues lining the patient's airway. This is recognized in U.S. Pat. No. 5,007,408 (Ieoka), which regulates the light in a similar system by using color-separating filters. The light is pulsed for predetermined time intervals through an iris-controlled circuit to reduce the heat that is generated, thereby keeping the temperature slightly below tissue damaging levels. U.S. Pat. No. 5,005,573 (Buchanan) provides a light emitting endotracheal tube connected to, and controlled by, an external oximeter.

Light emitting systems are often used to detect irregularities in a duct, vessel, organ or the like. U.S. Pat. No. 4,248,214 (Hannal et al.) provides an illuminated urethral catheter to assist a surgeon in locating the junction of the bladder and the urethra to permit the proper performance of the Marshall-Marchetti-Kranz procedure. U.S. Pat. No. 4,782,819 (Adair) is representative of many patents using catheters for illuminating organs for internal inspection. For example, U.S. Pat. No. 5,947,958 (Woodward et al.) provides a system for the illumination of internal organs of a patient after insertion through, for example, the peritoneal wall. In that case, the light is provided for either imaging of the tissue surface or for delivering light for use in photodynamic therapy. However, such devices are not used for catheter placement, and are not the subject of the present invention.

In a conventional endoscope an illuminating light emitted from a light source outside the body is introduced into the body cavity through a light guide, which is inserted through a tube. The light is radiated onto tissue within the body cavity. In order to observe the tissue surface within the body cavity, the light, which is reflected from the surface of the tissue, is received and observed with the naked eye using an eyepiece, or is imaged by a television camera or the like. However, with conventional endoscopes the character of the viewed tissue, such as the venous circulation below the mucous membrane of the stomach or the minute structure of the venous system, cannot be seen. As a result, U.S. Pat. No. 4,898,175 (Noguchi) provides an imaging device in which a constant illuminating light is shined onto the tissue being observed through a catheter-type device inserted into the patient's body, permitting the interior of the tissue to be observed using a viewing device that images the light emitted to the outside of the body and processed by a signal processing device. The imaging of the '175 patent utilizes a solid state imaging device, wherein the illuminating light is sequentially switched among a variety of colors, or a single plate system, wherein a color filter is fitted to the front surface of the solid state imaging device to obtain a color picture image. However, the image is designed only to permit visualization of the tissue onto which the light is projected. It is not used as an optical guidance means for placing a catheter or scope quickly, easily and precisely within the patient's body.

U.S. Pat. Nos. 5,423,321; 5,517,997; 5,879,306; 5,910,816; 6,516,216; 6,597,941; 6,685,666 (Fontenot) provide multiple light guiding fibers of different lengths that are inserted into internal organs or vessels during surgery to reduce the danger of erroneously cutting into a passage or organ during surgery. The Fontenot catheter comprises an infrared-emitting flexible, polymeric, preferably round light guide encased in a flexible essentially infrared-transparent outer covering, such that infrared light is circumferentially emitted over the entire length of the duct, passage, etc of the patient, which permits the length of the passage to be viewed by the surgeon via an infrared photodetector. By placing a single emitter or line of emitters in the structure, the Fontenot patents operate to create a background of light against which the proximity of surgical instruments to organs or passages is determined by measuring intensity of light emitted, but the patents fail to provide or suggest precise and accurate information with regard to placement of the emitter in the patient.

U.S. Pat. No. 5,906,579 (Vander Salm et al.) and U.S. Pat. No. 6,113,588 (Duhaylongsod et al.) similarly describe methods for visualizing balloon catheters through the vessel wall under surgical conditions, specifically during cardiothoracic surgery. In these devices, the optical fiber is an independent entity, preferably inserted through one lumen of a multi-lumen catheter.

U.S. Pat. No. 5,540,691 (Elstrom et al.) provides a detection system consisting of a light source which is passed down the center of the intramedullary rod and a video system, sensitive to infrared light, which captures an image of the light transmitted through the transverse hole in the rod. The light simply shines out toward the surgeon who attempts to line up the drill by centering it on an area of light coming out of the hole. The infrared light is visualized using either a video system or night vision goggles to determine when the light intensity is centered around the drill.

U.S. Pat. No. 6,081,741 (Hollis) uses an array of inexpensive sensor elements to determine the center of an emitter that transmits light at a predetermined wavelength. For alignment purposes, the '741 patent provides the relative direction and relative amount of movement to rapidly achieve accurate alignment or orientation with regard to the emitted light spreading from the point source.

A series of related published patent applications 2002/0115922, 2003/0187360 and 2004/0019280 (Waner et al.) provide infrared monitoring of an intraluminal indwelling catheter, wherein optical properties are varied to form patterns to distinguish the light emitting catheter from adjacent anatomical structures.

Several patents, e.g., U.S. Pat. No. 4,784,128, use infrared sensors internally in the patient to locate heat generating body tissue, such as cancers. U.S. Pat. No. 4,821,731 uses a sound generating catheter to image internal features of the body.

Accordingly, as indicated above, prior efforts in this field have related primarily to protecting, managing, viewing, or treating parts of the patient's body. However, prior to the present invention, none of the prior art devices have been adapted to quickly, easily and precisely guide a catheter or other invasive delivery tube or device to an exact location within the patient. A need has existed, therefore, for a system and method to reliably locate and position invasive devices that overcomes these shortcomings without the requirement for x-rays or other cumbersome devices.

SUMMARY OF THE INVENTION

The present invention fulfills this need, among others by relying upon an emitted point or points of light being transmitted from the catheter within a patient to outside the body where it is detected and displayed to provide guidance of the catheter or similar device to a precise location within the patient. A system is provided comprising an optically-guided catheter having a proximal end, a distal end, and at least one lumen. A light-emitting means is coupled to the catheter, the catheter is inserted into place in the patient, and light is emitted as a point or points from a selected location, usually the distal tip, of the catheter to which it is coupled. The system further comprises an external detection device that detects the transdermally projected light, emitted by the light-emitting point, from within the patient, thereby indicating catheter placement within the patient.

In an exemplary embodiment, the provided system comprises a catheter or catheter-like device, a light source, a waveguide coupled to the light source for providing a light signal from the light source to the device such that the emitted light from the catheter within the patient can be detected from a location outside of the patient's body. The waveguide is coupled to an interior wall, an exterior wall, or embedded within a wall of a lumen of the catheter, or it may be coupled to the catheter but not affixed to the wall. An embodiment is provided wherein the waveguide comprises an optical fiber or multiple fibers in a fiber bundle. In yet another embodiment, light is generated by a light source located at the light-emitting point on the catheter and a waveguide is not needed. In either embodiment, the light source may be an LED or LD. The preferred emitted light is infrared or near infrared light, detectable by a photodetector. The system may further comprise one or more filters coupled to the photodetector. In addition, the system may also comprise an imaging device for displaying a visual image of the location of the light-emitting point of the catheter within the patient and/or a recording device for creating a record of the identified location of the light-emitting point.

It is an object of the invention to also provide an optically-guided medical catheter for use in the system described above, wherein the catheter comprises a light-emitting point from which light is emitted when coupled to the catheter, and wherein light emitted by the light emitting point is detectable by a detection device to indicate location of the light-emitting point within the patient.

It is also an object of the invention to further provide a catheter guidewire comprising an optical fiber as described above, wherein the fiber is embedded within a sufficiently rigid material so as to provide catheter guidance when the catheter is placed within the patient.

It is yet another object of the invention to provide a method of precisely placing a light-emitting point on an optically-guided catheter within a patient, the method comprising: 1)

inserting the optically-guided catheter into the patient; 2) emitting light from a light-emitting point on the catheter within the patient; 3) externally detecting light emitted from the light-emitting point on the catheter within the patient, wherein the light is transdermally projected from within the patient; 4) determining location of the light-emitting point within the patient, based upon the externally detected light; and 5) determining placement of the catheter within the patient, based upon location of the light-emitting point. The catheter devices, waveguides, wavelengths, lights sources, detection, imaging and recording devices associated with this method are as described in the system above.

It is also an object to provide a specialized method of this invention, wherein the optically-guided catheter is a Peripherally Inserted Central Catheter (PICC), inserted into a blood vessel leading to the heart of the patient, and wherein the emitted-light is emitted from the distal end of the PICC, said method further comprising moving the light-emitting point in proximity to the patient's heart and observing changes in pattern of emitted light as the light-emitting point approaches the patient's heart, wherein in proximity to the heart, the emitted light fluctuates in intensity synchronously with heart beats, thereby indicating the location of the distal end of the PICC within the patient's vessel in relation to the patient's heart. Also provided are additional methods comprising observing a marked occlusion of emitted light from the distal end of the PICC when the PICC end is advanced within the vessel and enters into the patient's heart, observing return of the emitted light to its non-occluded state when the distal end of the PICC is withdrawn into the vessel from the heart muscle; and based upon observations of the qualitative changes in the emitted light in the optically-guided PICC in proximity to the heart, rapidly confirming placement of, or changing placement of, the optically-guided PICC in the patient.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE DRAWINGS

For the purpose of illustrating the invention, there is shown in the drawings one exemplary implementation; however, it is understood that this invention is not limited to the precise arrangements and instrumentalities shown.

FIG. 3A shows an optical fiber embedded in the wall of a catheter. FIG. 3B shows an optical fiber coupled to the outer wall of a catheter. FIG. 3C shows a catheter incorporating a plurality of optical fibers in accordance with an exemplary embodiment of the present invention. FIG. 3D shows an optical fiber residing in a lumen of a dual-lumen catheter. FIG. 3E shows an optical fiber coupled to the inner wall of a catheter. FIG. 3F is a cross-sectional view of an optical fiber in a guidewire in accordance with an exemplary embodiment of the present invention.

DETAILED DESCRIPTION OF CERTAIN EMBODIMENTS OF THE INVENTION

Figure 1:
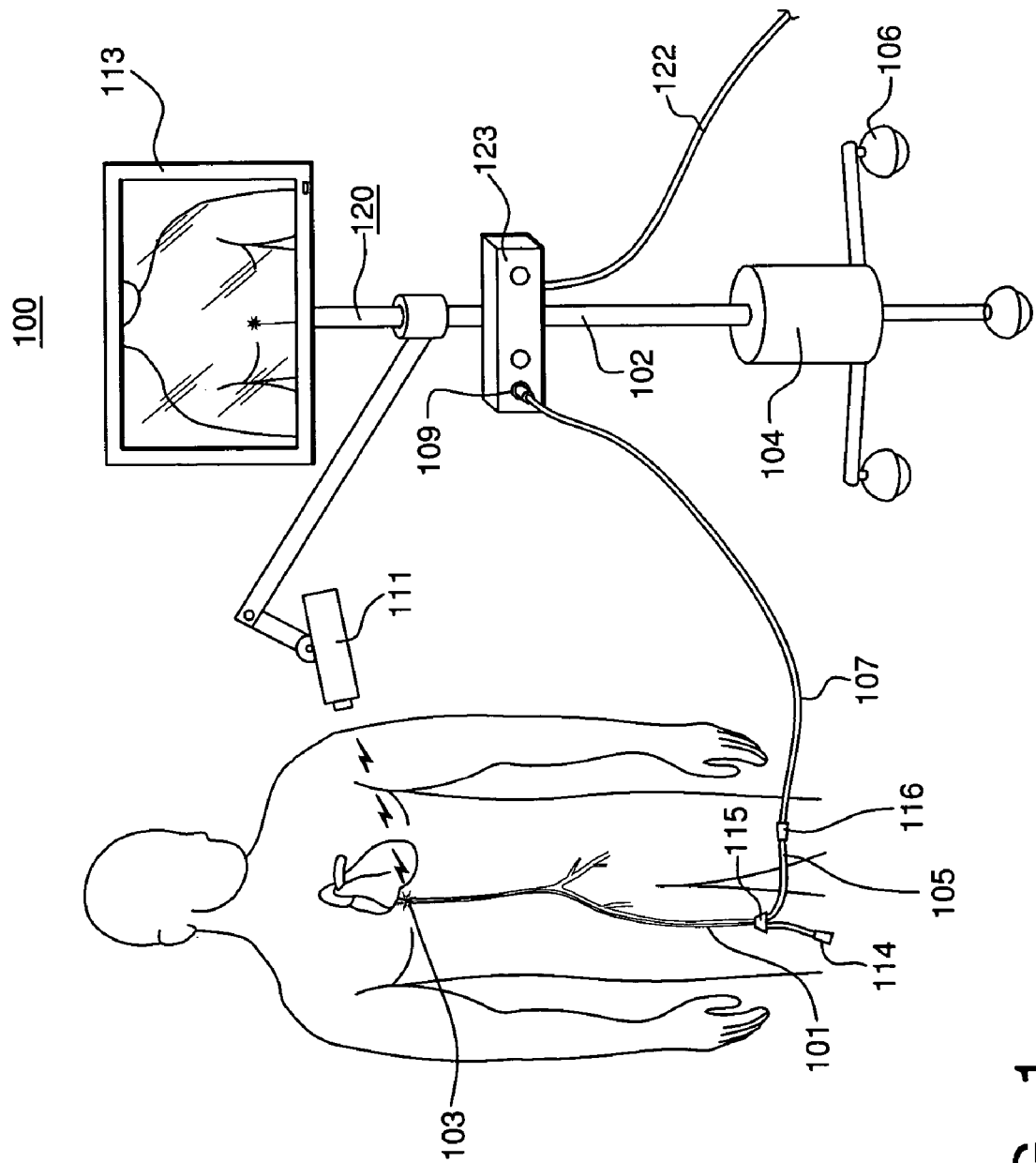
FIG. 1 illustrates a system for positioning an invasive device in accordance with an exemplary embodiment of the invention.

The present invention is described to permit quick, reliable, and precise placement of an optically-guided catheter (or other catheter-like device) into organs, vessels, ducts or passages within a patient. Through detection of the lighted distal tip, the invention allows for the tracking of the light-emitting, optically-guided catheter as it is advanced into a patient and for the precise identification of the tip (or alternative portion of a catheter) for accurate final placement of the catheter. The light emitted from the optically-guided catheter introduced into the patient is detected ex vivo and displayed externally by a coordinated viewing/recording device. The light-emitting catheter of the present invention is not limited to one particular type of catheter, nor is the system comprising the catheter restricted in use or location. Rather, it is useful for all situations in which precise placement of a catheter is necessary, or when reconfirmation of the precise placement of an indwelling catheter is beneficial or desired. The description below and several examples are provided to illustrate the utility of the present system and method.

Catheter

The present invention establishes an optically-guided property of catheters, permitting precise placement of the thus-improved catheters, while leaving the basic function of the catheter unaltered. Accordingly, the optically-guided catheter element of the present invention comprises all medical catheters, including tube-like or catheter-like devices recognized in the art, having a light-guide and/or other functionalities that permit a point of light emitted from within the patient to be detected and displayed outside of the patient. This provides to the clinician an ability to precisely place the distal end, or other selected region(s) of the device.

The term "catheter" is used herein to collectively denote all invasive or non-invasive types of catheters and catheter-like devices, e.g., peripherally inserted central venous catheters (PICCs), coronary catheters, pulmonary artery catheters, epidural catheters, central venous catheters, peripheral vascular catheters, etc., as well as alternative catheter devices (e.g., feeding tubes, endotracheal tubes, urethral catheters, and the like). Feeding tubes have recently been classified as being non-invasive catheters. For ease of reference, therefore, the term "catheter," is herein applied to all catheters and tube-like or catheter-like devices, even though technically they may not always be called a catheter per se, that are inserted into a patient for protecting, managing, viewing, or treating parts of a patient's body, and with which the optically-guided system of the present invention quickly, easily and precisely permits placement at an exact location within the patient. Thus, as used herein, the term further includes catheters that are used as delivery devices, such as for the delivery of a stent and/or other medical device to a precise location in the patient.

For discussion purposes, the catheter has a proximal end and a distal end, and comprises at least one lumen internally within the catheter and extending longitudinally for the entire length of the catheter. Catheters having a plurality of parallel lumens, of the same sizes, shape or internal diameter, or different, are known in the art. The distal end of a catheter is inserted into the patient via an orifice or through the skin in accordance with recognized medical practices, depending on the intended purpose of the catheter. By manipulating the proximal end of the catheter, the clinician maneuvers the distal end to a precise location in the patient, leaving the proximal end of the catheter at the point of entry or extending externally beyond the point of entry into the patient, or placed subcutaneously. In the preferred use, the distal end of the optically-guided catheter is precisely positioned in the patient, although other uses of the device will be described separately.

The physical characteristics of the catheter range from flexible to rigid, and the selection of the catheter by the practitioner depends upon its intended purpose. When selecting an optically-guided catheter, the practitioner's criteria for choice need not change from what would normally be selected simply because of the addition of the present optically-guided system. For example, but without intended limitation, an endotracheal tube would typically be selected from a material characterized as semi-rigid to flexible. By comparison, again only as a non-limiting example, when the catheter is intended to function as an orogastric tube the skilled practitioner would select a catheter constructed of different materials and of a much larger diameter, as compared to, for instance, a narrow gauge arterial or venous catheter. The vascular catheter, for example, requires greater flexibility and resilience.

Consequently, catheters are known to have a wide range of characteristics, including many different dimensions and proportions. Some catheters are of fixed length; others like PICCs are cut to length. Moreover, the catheter may be constructed having one or more lumens. Such varied needs of the patient, as well as the range of physical characteristics and the selection of the catheter itself, are well within the scope of the practitioner of ordinary skill having experience in using catheters in the medical arts. Accordingly, a more detailed discussion of the physical characteristics of the catheter and the basis for its selection by the skilled practitioner is believed to be unnecessary for the practice of the present optically-guided catheter system.

Waveguide

The term "waveguide" is used herein to refer to a light conductive element that provides light of the necessary wavelength(s) to be used in connection with the catheter element of the system of the present invention. The waveguide allows transmission of light into the body so that it can be detected externally, or outside the body. This allows for the precise placement of the optically-guided catheter. The terms "optical-guide" or "light-guide" are also encompassed by the term waveguide.

The waveguide is terminated with a distal light emitting end just short of the distal end or tip of the catheter (within 0.01 to 1.5 cm, preferably 0.3 to 1.0 cm, preferably ≦1.0 cm, preferably ≦0.75 cm, preferably ≦0.5 cm). Nevertheless, the terms "distal end" and "tip" are used herein with the understanding that the waveguide ends just short of the actual distal end or tip of the catheter as defined in the preceding sentence. As a result, the light radiates outward from within the catheter and is diffused by the catheter material (typically transparent or translucent plastic), making it multidirectional. In an alternative embodiment the waveguide may reach to or slightly beyond the end or tip of the catheter, but in such an embodiment the waveguide end would need to be coated or insulted to protect it from abrasion or damage during handling or while in use in the patient. Advantageously, such additional protection is not needed for the end of the waveguide in the embodiment in which the waveguide stops just before the end of the catheter.

In certain embodiments, if the waveguide is terminated at a different point on the catheter, the light still passes multi-directionally through the catheter material. Preferably the light shines outward circumscribing an approximately 360° radius from the tip of the catheter, or other selected point on the catheter. Note that rather than repeat in each instance that other points may, in some cases, be selected on the catheter for precise placement in the patient by the optically guided system, it is understood herein that each reference to the "distal end" or "tip" of the catheter shall also encompass other selected locations on the catheter, both in the singular and in the plural.

The light itself becomes fully omni-directional as soon as it enters the tissue surrounding the inserted catheter. Thus, a diffuser may be added to the end of the optical fiber for regulatory purposes, although it may not be necessary to enhance the present system. In another embodiment, the distal end or selected portion of the catheter is etched or constructed of plastic containing reflective particles if greater diffusion is needed. Regulatory requirements are based on the light in any given direction that can be imaged by the eye and/or the absolute intensity of the light in mW/cm2 at a specified distance from the source (fiber tip, LED, independent light source, etc).

In certain embodiments of the invention, fiber optics are used to provide light transmission through flexible transmissive fibers to direct the light to the distal end of the optically-guided catheter. In that case, the waveguide is a single optical fiber or several single fibers, or a bundle of light conducting fibers, or any combination thereof (collectively referred to herein simply as the "optical fiber"), affixed to the catheter, as will be described in greater detail below. Each optical fiber comprises a light carrying core and cladding which traps light in the core. Typically each fiber is a two-layered glass or plastic structure, with a higher refractive index interior covered by a lower refractive index layer. One of ordinary skill in the field of fiber optics would be familiar with and could readily select from the range of construction types, from continuous gradient to steps in refractive index.

Although, using either diffusive plastic on the tip of the catheter or etching the fiber would be more effective and less expensive, in an alternative embodiment multiple fibers of different lengths are employed, i.e., a fiber bundle consisting of very thin waveguides. More specifically, multiple small diameter (25 to 50 microns) fibers are assembled, twined, and then terminated at the distal end of the light-emitting catheter, particularly for three dimensional imaging of the catheter tip position and the intervening tissue In addition, the terminus of each small fiber in the bundle may be cut at an angle so as to direct the near-infrared light in a complete circle from the end of the emitting catheter. A reflector can also be placed at the distal end of the light-emitting light guided catheter to reflect any light energy not initially scattered to the outside of the patient, thereby increasing the efficiency of the light being emitted transdermally from the waveguide. These embodiments in which a bundle of fibers are used are for simplicity also referred to herein as an "optical fiber."

Any design or size of optical fiber or waveguide is suitable in the present invention, so long as (1) it provides light of the necessary wavelength and characteristics to be viewed through the skin from within the patient, and (2) it is sufficiently small to fit on or within the catheter or catheter wall and to permit the catheter to function without impeding its intended purpose, and (3) it is compatible with the presently described system. The waveguide is selected to produce a wavelength compatible with a device used to view and/or record the light shining from within the patient when the light is activated.

There are several general methods for coupling an optical fiber to the catheter. In one embodiment, the optical fiber is included within or coupled to the interior wall of the catheter. The "interior" of the catheter refers to the lumen side of the catheter wall, or if there are multiple lumens in the catheter to the lumen side of the wall of at least one lumen within the catheter. This lumen may be dedicated to just the optical fiber or it may reside in only part of the lumen, permitting the remainder of the lumen to remain available for other purposes. In another arrangement, the optical fiber is joined to or formed within the interior wall of the catheter during construction, or alternatively joined to or formed along an exterior wall (i.e., the outside surface) of the catheter during construction. Each of these means of attachment is intended to "couple" the optical fiber to the catheter.

In another arrangement, the optical fiber is later added to the interior surface of the catheter wall by, for example, blowing it into the catheter lumen. The fiber, in one embodiment, is further fixed in place (e.g., by gluing) on the interior wall of the catheter lumen. The attached optical fiber is then coated in place on the wall with a protective (e.g., plastic) coating that effectively isolates the optical fiber from contact with body or other fluids that may be transmitted through the catheter lumen, and protects it from abrasion as devices, such as a guidewires, stents etc. pass through the catheter. A similar process can be used to fix the optical fiber to the outside wall of the catheter. As above, each of these means of attachment is also intended to "couple" the optical fiber to the catheter, as is the insertion of the fiber into the catheter lumen without fixing.

Alternative Embodiments

Waveguide as Guidewire

In one embodiment, the optical fiber is attached to a catheter guide-wire in a manner similar to that which was just described, so that the optical fiber and the guide wire become one. Such catheter guide wires are well known in the art. In a variation of this approach, the guide wire is not a wire per se, but rather, it is a metal coating applied over the optical fiber to convert it into a guide wire/optical fiber element, which then has the physical properties desired for both providing a light guide for viewing the catheter tip and for providing stiffness and guidance as the catheter is positioned within the patient.

In another arrangement, the optical fiber comprises the core of a standard guide wire; whereas, in yet another arrangement, the optical fiber is attached to the outside of the guidewire, with or without protective coatings, to make the unit function as one.

In yet another embodiment, the guide/guidewire is introduced into the patient and the distal tip of the waveguide/guidewire is properly positioned using the system as previously described. However, in this situation a catheter, wherein the material at the tip is too dense to allow transmission of light, is then slid into place over the waveguide/guidewire. Thus, the position of the catheter can be identified as the emitted light is quenched as the catheter covers the waveguide (and accordingly, the transmitted light).

In a further embodiment, a catheter (such as, a PICC that has been cut to length) comprising a waveguide/guidewire, is introduced into the patient, advanced until the distal tip of the catheter is properly positioned in the patient. The position of the catheter is confirmed by using the detector in the manner previously discussed, but then the waveguide/guidewire is withdrawn from the catheter, leaving the catheter precisely as placed.

In still another embodiment, the waveguide/guidewire is introduced into the patient and the distal tip of the waveguide/guidewire is properly positioned using the system as described. And then the catheter, also containing a waveguide, is slid over the guidewire into position in the patient. The catheter waveguide is then distinguished from the waveguide/guidewire by flashing one, or the other, emitted light or by using a different wavelength for each waveguide and detecting each separately, or by using a detector capable of broadly detecting the range of the selected wavelengths.

Light Emitter(s)

Light emitter(s) are a key element in the present optic system. A light emitting element converts an electrical analog or digital signal into a corresponding optical signal, which in the optical fiber system of the present invention provides a light signal that can be injected into the fiber. The light emitter is an important element because it is often the most costly element in the system, and its characteristics often strongly influence the final performance limits of a given link.

The most common devices used as the light source in optical systems are the light emitting diode (LED) and the laser diode (LD), typically a solid state LD. Each is a semiconductor device that emits coherent light when stimulated by an electrical current, as will be discussed in greater detail below.

Selected Power and Wavelength

The light transmitted by or from the optically-guided catheter of the present invention falls in the near infrared region of the spectrum (~620 nm to 1500 nm), typically having an emission less than 5 nm wide and light energy in the range of 1 to 100 mW. The selected power may be less than 50 mW, less than 30 mW, or even less than 10 mW, so long as the transmitted light can be detected transdermally. The best results are usually achieved by coupling as much of a source's power into the fiber as possible. The key requirement is that the output power of the source must be strong enough to provide sufficient power to the photodetector at the receiving end, yet it must remain low enough so that tissue is not damaged and the patient is not harmed or caused unnecessary discomfort. Optimally, the selected power level produces little heat, and little or no risk to the patient. In a fiber optic system, selection of power level must consider fiber attenuation, coupling losses and other system constraints.

A near-infrared light source is preferred in the present invention because there is less absorption of the light by chromophors in the tissue and less light scattering by small particles and other structures within the tissue, as compared with the effect when shorter wavelengths are used. The infrared region of the spectrum includes much longer wavelengths, and through-out most of that wavelength range, tissue has quite high absorption. Preferably the selected transmitted light is 620 nm to 1100 nm, more preferably 650 nm to 980 nm, more preferably 700 nm to 930, more preferably 750 nm to 930, more preferably 750 to 850 nm. Moreover, these particular ranges of wavelengths of light are selected because human skin readily transmits near-infrared and infrared light, and the underlying or subcutaneous structures attenuate infrared light. Muscle fiber tends to scatter the light, whereas it is absorbed by oxygenated and deoxygenated hemoglobin in the blood stream. See, e.g., Anderson et al., J. Invest. Dermatol. 77(1):13-19 (1981).

Some wavelengths within the stated range perform better than others. For example, shorter wavelengths do not penetrate very far into the tissue. From 620 nm to about 700 nm the light is considered "visible" because the eye can detect it, although sensitivity of the eye falls rapidly with increasing wavelength of the light being detected. Accordingly, by coordinating the selected wavelength with the photodetector of the present system, optimal detection of the transdermally-transmitted light is provided. While the transdermally-transmitted light may also be viewed directly by the practitioner at certain wavelengths, the present invention provides a level of detection, sensitivity, and accuracy that could not reliably be provided by a practitioner using unaided visual observation alone.

Light Sources

In a preferred embodiment, the light sources are LDs or super-luminescent diodes (SLD), since they are known to provide sufficient brightness for the present invention when coupled into a small optical fiber. In the alternative, selected LEDs, preferably surface-emitting LEDs (SLEDs) also provide sufficient light to be seen through the skin of the patient, and are more economical. The LEDs of the present invention are those suitable for use in fiber optics, not the more common indicator LEDs used in common appliances. The optical LED advantageously transmits wavelengths in the near infrared (because the optical loss of fiber is lowest at these wavelengths), and the LED emitting area is generally much smaller than in the indicator LED, thereby allowing the highest possible modulation bandwidth and improved coupling efficiency with small core optical fibers.

In fact, while there are differences between a LD and an LED, when operating below their threshold current, LDs act as LEDs. Accordingly, it is intended that the present invention applies to any or all solid state light sources having sufficient power when coupled into the optical fiber, thereby providing light that is transmitted through the patient and viewed through the skin of the patient to provide precise placement of the attached device. This is intended to include light sources developed in the future that are capable of generating the proper light output. While the utility of the invention is demonstrated using a variety of light sources, further source enhancements can be made by one skilled in the art as guided by these teachings.

A preferred light source is typically a commercially available LD or LED, having a spectral peak centered at about 830-920 nm. The light emitting diode laser is a solid state device employing a p-n junction in a semiconducting crystal. A narrow spectral emission band is produced by the recombination of electrons and holes in the vicinity of the junction when a small bias voltage is applied in the forward direction. The peak wavelength is the wavelength at which the source emits the most power, in this case within the near infrared range. When an optical fiber is used in the present invention it is matched to the wavelengths that are transmitted with the least attenuation through optical fiber. Ideally, all light emitted from an LED or LD would be at the peak wavelength, but in practice light is emitted in a range of wavelengths centered at the peak wavelength. This range is referred to as the "spectral width" of the source. The narrow band source of light produced by the LD can be readily coupled into small diameter (less than 500 micron core) optical fibers.

LEDs are complex semiconductors that convert an electrical current into light. The conversion process is fairly efficient in that it generates little heat compared to incandescent lights, but it is not as powerful as a LD. LDs and LEDs are advantageous for use in the optically-guided catheter because they are small yet they possess high radiance, i.e., they emit a lot of light in a small area. Their size is comparable to the dimensions of an optical fiber. They have a very long life, offering high reliability. Moreover, they can be modulated (turned off and on) at high speeds.

The primary difference between the two for the present purpose is primarily that surface emitter LEDs have a comparatively simple structure, while still offering low-to-moderate output power levels. SLEDs emit light in all directions, which is beneficial for the present invention.

The spectral location of the peak output wavelength of the LD is determined by selecting one of a variety of alloy semiconductor materials, such as GaAs, InGaAs or SiC, and by varying the composition of the selected semiconductor. A suitable source within the preferred range of the present invention is a narrow band, commercially available GaAs or GaAlAs (gallium arsenide or gallium aluminum arsenide, respectively) light emitting diode laser, having a peak output wavelength at 830 to 905 nanometers and a bandwidth of only a few nanometers (e.g., Hitachi model HE 8801 GaAlAs IRED). Longer-wavelength devices generally incorporate InGaAs or InGaAsP (indium gallium arsenide or indium gallium arsenide phosphide, respectively).

Because an LED light source of appropriate wavelength and energy produces light of a much wider spectral width than a LD, a wider bandpass filter may be required on the photodetector. See Filters below under the heading Detection Devices. The optical bandwidth of the light becomes important as it becomes greater than about 40 nm due to the increase in room light that passes through the filter and onto the photodetector. Although this background illumination is increased when using filters passing a wider range of wavelengths, the resulting decrease in signal to noise can be compensated by using modestly higher power light sources.

In the fiber optic system of the present invention, the LD or LED light emitting devices are mounted in a package that enables an optical fiber to be placed in very close proximity to the light emitting region in order to couple as much light as possible into the fiber. In some cases, the emitter is fitted with a tiny spherical lens to collect and focus all possible light onto the fiber. In other cases, a fiber is "pigtailed" directly onto the actual surface of the emitter. A pigtail is a short length of fiber attached to a fiber optic component, such as a laser or coupler. When a proximity type of coupling is employed, the amount of light that will enter the fiber is a function of several factors: the intensity of the LED or LD, the area of the light emitting surface, the acceptance angle of the fiber, and the losses due to reflections and scattering The intensity of an LED or LD is a function of its design and is usually specified in terms of total power output at a particular drive current. Sometimes this figure is given as actual power that is delivered into a particular type of fiber. All other factors being equal, more power provided by an LED or LD translates to more power "launched" into the fiber. The amount of light "launched" into a fiber is a function of the area of the light emitting surface compared to the area of the light accepting core of the fiber. The smaller this ratio is, the more light that is delivered into the fiber. The acceptance angle of a fiber is expressed in terms of numeric aperture (NA), defined as the sine of one half of the acceptance angle of the fiber. Typical NA values are 0.2 to 0.8 which correspond to acceptance angles of 11 degrees to 46 degrees (which should match the NA values). Optical fibers will only transmit light that enters at an angle that is equal to or less than the acceptance angle for the particular fiber. Other than opaque obstructions on the surface of a fiber, there is always a loss due to reflection from the entrance and exit surface of any fiber (referred to as the Fresnell Loss, and is equal to about 4% for each transition between air and the glass or plastic fiber material). There are special commercially available coupling gels that can be applied between glass surfaces to reduce this loss when necessary.

The light generation systems may further require or benefit from the use of recognized enhanced signal regenerators, signal repeaters, or optical amplifiers, such as EDFAs, in order to maintain signal quality. When fiber optics are applied, a fiber optic amplifier may be used, i.e., an all optical amplifier using erbium or other doped fibers and pump lasers to increase signal output power from the optical fiber without electronic conversion.

Pulsed Light

In certain embodiments of the invention, the light source is pulsed to both decrease the total light intensity needed and to facilitate detection of the flashing emitted light. For example, pulsed light could facilitate the detection of a dense organ, such as the heart (not to be confused with the pulsating intensity of the transmitted light described in Example 2 as the optically-guided catheter approaches the heart). Pulsed light has a number of advantages over a constant beam of light emitted from the catheter, including, but not limited to, significantly reducing the power needed to transmit the light because it is 'on' only for a short burst. This also means that significantly less heat is generated that could damage the surrounding tissue in the patient. This reduces or eliminates light-based safety concerns associate with the use of the present invention.

It is well recognized in the art that a pulsed or flashing signal of known characteristics (pulse width, frequency, time of pulsing, etc.) can be detected and measured much more accurately and against noisier backgrounds, as compared to continuous signals. Moreover, the photodetector and light source can be frequency and time locked. This allows the optical signal when the light is 'off' to be subtracted from the signal when the light is 'on' prior to amplification. This dynamic subtraction of the background suppresses contribution due to room lighting, since presumably the room or background light is the same whether the transmitted near-infrared light source is 'on' or 'off.' This substantially improves the recognition of signal over noise.

Using 1 millisecond pulses with a frequency of 100 Hz, there are 100 pulses per second (10% duty cycle). If the light source is 100 mW, the duty cycle of 10% gives an average power of only 10 mW in consideration of regulatory purposes, whereas the photodetectors 'view' the signal from a 100 mW source. The pulse frequency can, therefore, vary widely, depending on the light source/photodetector used. This can range from LIght Detection And Ranging (LIDAR) frequencies (MHz) ranging as low as 1 Hz, although optimal frequencies may be in the 100 Hz and 10 kHz range. The pulse widths are adjusted to values that give preferred duty cycles of between 1% and 10%. Notably, a 1 microsecond pulse at 100 kHz equals a 10% duty cycle, whereas a 100 microsecond pulse at 100 Hz is a 1% duty cycle.

Moreover, the signal can be accumulated (summed and/or averaged) from many different pulses to provide greater sensitivity (increased signal to noise ratio) by the square root of n, wherein n is the number of pulses averaged.

Multiple Wavelengths

In yet another embodiment of the design, the light source consists of several wavelengths or a continuum of wavelengths. Since different tissue types, e.g., muscle, adipose, lung etc., have very different absorption and light scattering properties, the differences in intensity measured at a variety of different wavelengths is analyzed to show the position of the catheter tip in three dimensions. With application of appropriate known mathematical algorithms describing the scattering of light by tissue at each wavelength, three dimensional renderings made of the absorption and scattering properties of the tissues between the catheter tip and the cutaneous surface where the measurements provide a 3-dimensional "image" of the internal structure of the body. The spatial resolution obtained for structures between the light source and the body surface are dependent on the number of measurements made and other experimental parameters.

Light Detection and Imaging Devices

A photodetector is a device comprising a photodiode, or a photodiode and signal conditioning circuitry, that converts light to an electrical signal. In the present case, the light is transmitted to the photodetector from the optically guided catheter in a direct line to the nearest transdermal area on the patient, as set forth above. The conversion of light to an electrical signal permits imaging and recording of the light. Various different types of photodetectors, such as near-infrared photodetectors, photomultipliers, photodiodes and avalanche photodiodes, cameras, and the like are used as imaging devices of the present invention. CCD arrays, singlely, or in groups, may be used to determine the intensity and position of the emitted light. The detection system can be coupled to any of several different additional devices for enhancing and reporting the position of the detected light on the surface of the patient's skin to the operator.

Photodetection devices are well understood and readily used in the art, and further discussion of photomultipliers, photodiodes, including silicon PIN photodiodes, and avalanche photodiodes (APD), including silicon APD, are not believed to be necessary for the practice of the present invention by the skilled practitioner. All are herein included; although at low frequencies and at low, but not ultralow, signal levels, a PIN photodiode is often preferred, whereas at other light levels, avalanche photodiodes may be preferred. For example, a wavelength range of 200 to 1100 nm is associated with silicon photodiodes. However, as recognized by one of skill in the art, other photodiode compositions have different wavelength sensitivities, and such an individual will know how to select the preferred detection sensitivity or capability.

Filters

Photomultipliers and image intensifiers are generally less sensitive in the near-infrared wavelengths than they are in the visible region of the spectrum. As a result, filters may be desired for all photodetectors of the present invention if there is significant room lighting present. In one embodiment, the detection device is covered with an appropriate filter or filters. The contrast ratio or signal-to-noise-ratio (SNR) drives the spectral performance of both the light source and the filter in a synchronized manner. For example, using a narrow band light source, such as an LED, and a filter having passband(s) which are very narrow (a few nanometers FWHM) and highly transmitting (>80%) will yield a good and workable SNR.

Even if the light transmitted from the optically-guided catheter includes a range of wavelengths when used in a patient, in practice, the distal end of the catheter is treated as a single light emitting point. The light issuing from the body is typically a nearly round spot, herein referred to as a "point of light,' although when a plurality of emitted lights are used in sufficiently close proximity to each other in or on the catheter (i.e., in a feeding tube with multiple openings), each represents a single point of light, but collectively, they may be detected as an apparent length or bar of light. The place on the body surface at which the maximal light emission occurs is approximately that which is closest to the tip or selected region of the catheter. This is because the light intensity is strongly dependent on the distance from the source (tip of the catheter) to the body surface, i.e., the distance it has to travel (diffuse) through tissue. Thus, the point of light from the catheter is detected transdermally on the external surface of the patient at a location directly in line with the transmitted light from the distal catheter tip (or other selected point) within the patient. In general, the contribution of other ambient lighting (admitted noise) increases directly with the increased width of the optical filter bandpass.

Depending on the ambient room lighting, the background lighting can be either lower than visible light (fluorescent lamps) or higher (operating lamps, tungsten filament based lighting in general). Accordingly, the operator advantageously uses filter(s) to enhance the quality of light recognized by the detection system of the present invention. In doing so, the wavelengths of light reaching the photodetector are passed through the optical filter that removes (to the extent possible) the background room light, preferably until the room light (interfering noise) is optimally no longer detected by the photodetector. However, in practical application the background illumination increases the total light falling on the photodetector, thus increasing the noise reaching the photodetector. In addition, commercial light sources tend to add to the noise. They are noisier at higher frequencies, since little effort is made at the commercial level to control modulations that occur too fast to be 'seen' by the naked eye. Fluorescent lights, typically used in medical facilities, for example, are modulated at frequencies of 180 and 360 Hz, and in addition they produce substantial amounts of higher frequency noise due to arc instabilities.

The background room light will interfere in proportion to the intensity of the wavelength used in the waveguide. Narrow band interference filters (e.g., 10 nm bandpass) having high attenuation (about 10-4 to 10-5) blocking wavelengths outside of the transmitted passband(s) will further improve the SNR, typically allow measurements in a fully lighted hospital room. Nevertheless, it is advantageous for the practice of the invention to turn off surgical lights and other particularly high intensity light sources.

To select the appropriate filter, in one embodiment, a narrow pass (<10 nm at half height) is preferred, although wider bandpass filters could be used. In the alternative, an interference filter having a peak wavelength centered at 780 nm (for a light source of 780 nm) can be used to cover the photodetector viewing surface. The value of $\leqq 10$ nm is selected, by example only, to allow some variation in the LD wavelength, while at the same time minimizing the amount of extraneous light (other than the light transmitted from the LD or LED) that passes through the filter(s) to the photodetector. Of course, if other wavelengths of light are used, an appropriate interference filter is selected that is centered at about that wavelength.

Filters for enhancing near-infrared light are well known in the art and are commercially available. They can be readily selected by the practitioner, depending on the existing background light and wavelength selected for transmittion. Since there is less extraneous ambient infrared or near-infrared light with which to contend, such filters enhance the detection capability of the selected near-infrared light, and benefit the intended coordination of the transmitted wavelength with the detection device.

Detection systems, such as those used in night vision goggles (NVGs) and other image intensifying systems, exclude the background visible light to the greatest extent possible, permitting the near-infrared light of interest to be more easily detected. As a result, for example in night vision goggles, it is really the filter(s) that makes near-infrared light visible to the practitioner or detection device over the visible light.

While it is understood that detection systems of the present invention are not limited to NVG photodetectors, and they are, in fact, more cumbersome than other detection systems, they do provide an easily understood example of the use of filters on a near-infrared detection device. For example, such near-infrared night vision goggles or an equivalent detection device having filters coordinated with the wavelength of the transmitted light, may be employed in the system to display and follow the progress of the transmitted light of the optically-guided catheter from the site of entry to the chosen location in the patient. With the necessary filters in place, the detection device, therefore, amplifies or multiplies the emitted light, particularly at low levels of transmitted near-infrared light.

The light absorbing filter can operate based on either its substrate per se (such as a selected glass or plastic) and/or an optical coating over the substrate; whereas, an interference filter is typically derived from the coating. The specific filter for accomplishing a particular spectral sensitivity may be selected without limitation by one skilled in the applicable art as guided by these teachings. Ambient light may also be excluded from the spectral range of interest by performing the method of the invention in an environment suitably shielded.

Because of the differences in absorption characteristics of venous blood, arterial blood, and abnormal structures as compared to skin, bone and surrounding muscle and fatty tissue, the location and arrangement of veins, arteries or other structures can be visualized using an imaging system in the present invention of appropriate spectral sensitivity. In the alternative, a combination of filters are used to select the spectral range of viewing into narrow transmission band(s) to allow use of system in daylight, to differentiate venous from arterial blood or to exclude noise or other radiation not contributing to the desired image. Filters may also be used in conjunction with an imaging system to narrow the spectral range of viewing or to exclude light that might interfere with the visualization of specific subcutaneous structure of interest. It is nevertheless important to ascertain, regardless of the type of near-infrared photodetector that is employed, that intervening surgical instruments, sponges and the like, do not mask the transmitted light emission from the optically-guided catheter through the patient to and through the skin.

Additional Components of the Photodetector System

In a selected embodiment, an emitter control circuit controls the energy to the optically-guided catheter. A safety detector in another embodiment determines the integrity of the coupling between the near-infrared emitting catheter and its control circuit and/or the continuity of the infrared emitting light guide. The addition of an audible system can be also employed, for example to warn of errors in the connection of the energy source supplying light to the light-emitting catheter, e.g., inconsistencies in the actual wavelength or intensity provided as compared with the selected wavelength or intensity. Audible signaling is just one way of providing non-visual information to the operator, thereby permitting the operator to look toward the patient while, for example, passing a photodetector over the patient's body.

In an alternative application of the optically-guided system of the present invention, the near-infrared detecting light guide is physically coupled to an instrument employed for cutting, e.g., a laparoscopic electrocautery instrument. However, since cutting instruments are generally used with internal imaging systems, and the present light-guided catheter is not an internal imaging system, such instrumentation would probably not be used in conjunction with the optically-guided catheter to provide the precise placement of a cutting instrument.

In another embodiment, a visual light source video camera and monitor are employed with the system to provide a visual display of the light emitted transdermally to the outside of the patient's body from the organ, passage, duct, vessel or the like. A means of recording the images is further provided in an embodiment, although the images may be recorded or not, at the election of the operator. Because the imaging means resides outside of the patient's body, and the observation of the guiding light is made from outside of the body, the size of the imaging means is not limited, except by the convenience of the operator or institution in which the patient resides. A wide range of imaging devices can be operated in conjunction with the present system as would be recognized by one of ordinary skill in the art.

Other Considerations

The presently defined optically-guided catheter and system for its use can be practiced by anyone familiar with catheter placement, including health care persons in the field (military, rapid response teams and the like), and advantageously and reliably permits precise placement of the optically-guided catheter. No specialized facilities are needed, except for the availability of a photodetector device. The present system is particularly useful for precisely placing the catheter in trauma situations when a clear view of the catheter might not otherwise be possible, and for maintaining the catheter in position when the patient is being transported from one location to another, especially when movement of the patient could dislodge the placed catheter.

To assist the practitioner using the optically-guided catheter system in the treatment of a patient, methods for visibly displaying the detected, transdermally-emitted light, include displaying the detected image on a monitor or TV screen to view the real-time image or recorded image of the light spot emitted transdermally from within the patient. Advantageously, the displayed image shows the emitted light as it appears externally with regard to the patient, or the image can be zoomed to show just a localized area of the patient. In an alternative embodiment, a visible second point of light is directed from an external source to shine onto the patient at the location of the detected near infrared light being emitted from the optically guided catheter within the patient, thereby acting as a visible pointer for the practitioner, who would otherwise not actually see the near-infrared emitted light directly on the patient.

Similarly, different photodetectors may be used, including photodiodes, photomultipliers, avalanche photodiodes, and microchannel plates. For example, in one variation of the detection system, a sensitive microchannel plate imager or similar device is used to place a mini-display directly in front of one eye of the operator, thereby allowing the operator to look at either the patient, or at the display, as desired. When photodiodes or other single site photodetectors are used, they can be moved over the patient to detect the maximum point of the specific light emitted from the optical fiber. The sensitivity of the measurement is maximized by modulating the light at a specific frequency (such as 1000 Hz) and detecting only the photosignal of that frequency.

A camera controlling unit may be provided with an automatic gain control to adjust the contrast of the image, providing enhanced visibility to the practitioner. The presently described system can also be associated with an emitted audible and/or visual signal indicating signal strength, etc. as the photodetector(s) is passed over the patient.

Like any catheter, the light-guided catheter is sterilized prior to patient use. However, since it is already sterile as delivered to the hospital or practitioner, there are no additional or particular sterilization requirements at the hospital, although known guidelines must be followed to maintain sterility of the catheter. The photodetector device and other system components that do not touch the patient do not need to be sterilized prior to use, although in accordance with standard (regulated) medical practice, they are regularly cleaned and prior to each use they are wiped with a sterilizing solution.

The risks involved in using the present optically-guided catheter are no greater than those associated with any other catheter system in a patient, and actually the risks are far less because of the accurate placement of the present device. While fiber optic cable is immune to all forms of interference, the electronic receiver/photodetector is not. Because of this, normal precautions, such as shielding and grounding, should be taken when using electronic components of the present optically guided catheter system.

The "patient" of the present invention is any human or animal into which an catheter would be used. The patient can be healthy or diseased, from the smallest infant to a large adult. All will benefit from the advantages of the precise placement of the light-guided catheter of the present invention.

Operation of System

Referring to FIG. 1, an exemplary system 100 for positioning an invasive medical device is shown. It is understood, however, that the following discussion is intended to be instructive of one embodiment of the present optically-guided catheter system, but is not intended to be limiting of the present invention. The system is described herein with reference to precise placement of an optically-guided catheter, as defined above, that it is physically inserted into the patient or maintained in its indwelling position. In the embodiment illustrated in FIG. 1, the system is shown having a catheter 101 precisely placed within a patient's body. Catheter 101, as shown in FIG. 1, is a dual lumen catheter with a bifurcation 115 at the point where the lumens join and IV connector hubs 114, 116 on each lumen to allow for coupling to further tubing/equipment. Catheter 101 is inserted into an artery in the leg (groin) of the patient and travels into the chest cavity. However, the apparatus and methods described herein may be used in other locations with the body in accordance with standard medical practices for the selected catheter type for a selected purpose, some of which are further described in the Examples that follow.

Catheter 101 has a distal end 103 and a proximal end 105. A waveguide 107 is coupled to a light source 109 and inserted into proximal end 105 of one lumen of catheter 101. System 100 operates by using waveguide 107 to provide a light signal to distal end 103 of catheter 101, from which point the light signal is emitted. The signal is detected transdermally, outside of the patient's body, enabling the location of distal end 103 to be determined. For example, light source 109 generates a light signal, which is provided to waveguide 107. The waveguide 107 enters the catheter 101 at a waveguide entry point (e.g., via IV connector hub 116 in the embodiment illustrated in FIG. 1) external to the point where the catheter 101 enters the patient. The waveguide 107 provides a path for the light signal to travel to the distal end 103 of catheter 101. Operationally, the light signal is emitted from waveguide 107 at the distal end 103 of catheter 101, preferably 360° in all directions. The emitted light passes through the body of the patient and is detected by photodetector 111.

In the embodiment illustrated in FIG. 1, photodetector 111 is physically coupled to base unit 120. However, one of skill in the art will appreciate that various forms of photodetectors can be used, including hand-held photodetectors that are coupled via a wired or wireless connection to the base unit.

Base unit 120 forms the mechanical support for the various system elements. In an exemplary embodiment, base unit 120 comprises a frame 102 formed of a strong, lightweight material such as aluminum. The lower portion of frame 102 has a weighted section 104 to stabilize frame 102, i.e., to keep it from tipping. In an exemplary embodiment, frame 102 contains a plurality of castors or wheels 106 to allow for base unit 120 to be mobile.

In the embodiment illustrated in FIG. 1, system 100 is powered by a standard 110 V power source via power cable 122. Alternatively, one or more batteries are used to power the system for systems where increased mobility is desired. In embodiments that use battery power, the system 100 has an advantage in that it does not require proximity to an electrical outlet.

Light source 109 generates a light signal that is coupled to waveguide 107. In an exemplary embodiment, the signal comprises radiation in the near-infrared or infrared spectrum. Transmittance of radiation through the patient's body is typically higher for radiation signals having longer wavelengths. As a result, radiation in the visible light range (i.e., wavelengths of 400 nm to 620 nm) are subject to higher levels of absorption by the body tissue (e.g., hemoglobin and other pigments) of the patient, which would require higher power levels to cause the same signal level to reach photodetector 111. Thus, using radiation in the near-infrared or infrared spectrum (e.g., 620 nm to 1500 nm) allows for the system to operate at lower power levels. It would be apparent, however, to one of skill in the art that the techniques described herein could be used in conjunction with radiation of various wavelengths.

In this exemplary embodiment, the light source 109 comprises a LD that operates at a maximal power level between 10 mW and 100 mW. The LD generates a light output having a wavelength of 830 nm, which is coupled into the waveguide 107. Alternative light sources (e.g., super luminescent diodes, LEDs) may also be used, and will be apparent to one of skill in the art.

Figure 2:
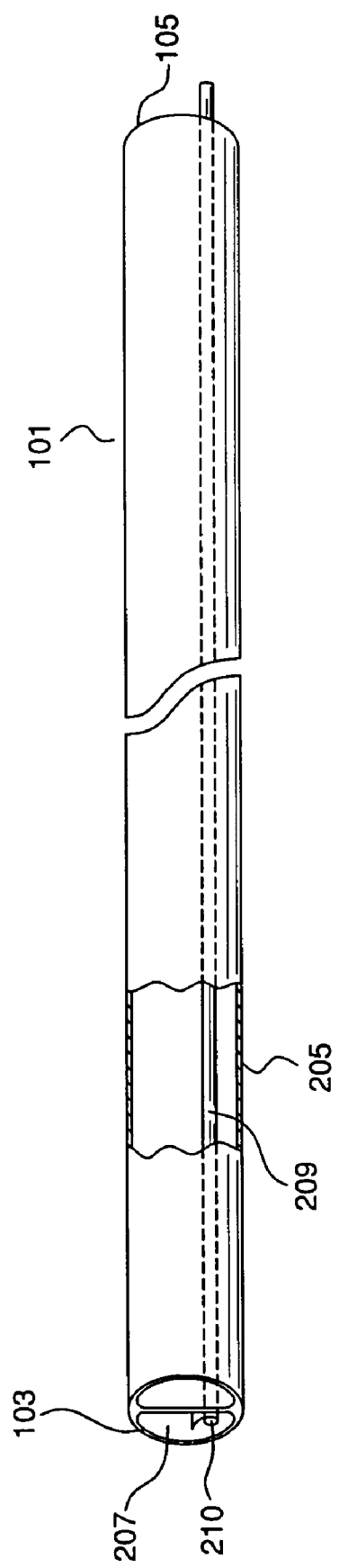
FIG. 2 illustrates a catheter for use in the system shown in FIG. 1.

Referring to FIG. 2, an exploded view of catheter 101 in accordance with an embodiment of the invention is shown. Catheter 101 has a distal end 103 and a proximal end 105, and a wall 205 that forms a tube enclosing an interior portion or lumen 207. An optical fiber 209 is coupled to the wall 205 along the lumen 207 to form the waveguide discussed with reference to FIG. 1. In the exemplary embodiment, the waveguide comprises an optical fiber with, e.g., a 100 micron core. Fiber 209 extends from a light source (109 of FIG. 1) into the catheter 101, entering at proximal end 105. The fiber extends the length of the catheter 101 and terminates at the distal end 103.

Figure 3A:
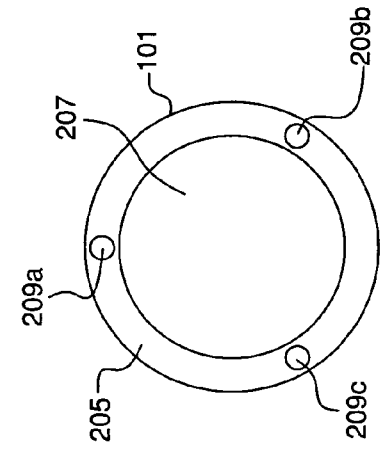
FIGS. 3A-3F are cross-sectional views of a catheter and optical fiber in accordance with an exemplary embodiment of the present invention.
Figure 3B:
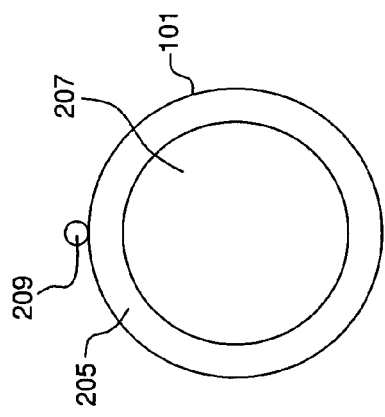
Figure 3C:
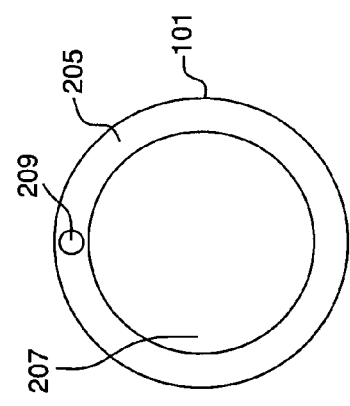
Figure 3D:
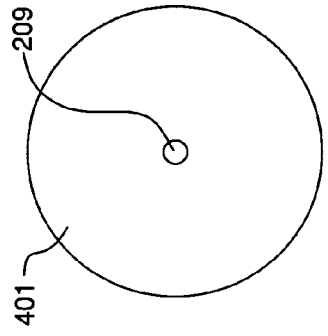
Figure 3E:
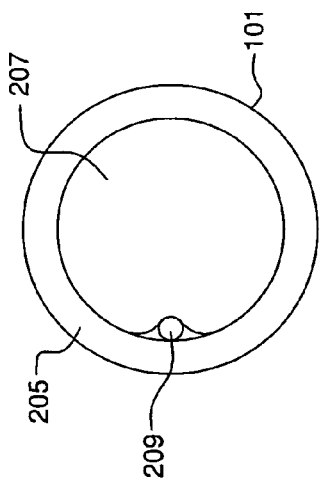

In the embodiment shown in FIG. 2, fiber 209 is coupled to the wall 205 in the interior of lumen 207. Alternatively, fiber 209 can be encapsulated into wall 205 of catheter 101, or fiber 209 can be coupled to the outside of the wall 205. Alternative configurations for locating fiber 209 with respect to wall 205 of catheter 101 are shown in FIGS. 3A through 3E. Referring to FIG. 3A, fiber 209 is shown encapsulated within wall 205. In FIG. 3B, fiber 209 is coupled to wall 205 the outside of catheter 101. Additionally, as shown in FIG. 3C, catheter 101 can include a plurality of fibers. Referring to FIG. 3C, first fiber 209a, second fiber 209b and third fiber 209c are encapsulated in wall 205. Additional fibers are further intended in other embodiments. The use of multiple fibers in a single catheter allows for radiation of differing wavelengths or differing modulation patterns to be used in a single catheter simultaneously. Additionally, the various fibers can be terminated at different locations along the catheter, which allows for tracking of more than one point along the catheter. This can be useful in determining whether a catheter is improperly inserted (e.g., has "doubled back" on itself). FIG. 3D illustrates fiber 209 residing in one of the two lumens 207a, 207b found in a dual-lumen catheter 101. In FIG. 3E, fiber 209 is coupled to the interior of wall 205 of catheter 101. Fiber 209 can also reside within lumen 207 without being coupled to the wall 205 of catheter 101. Multiple other configurations are possible, and would be apparent to one of skill in the art.

Figure 3F:
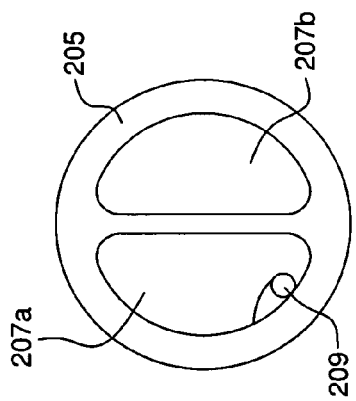
Figure 4:
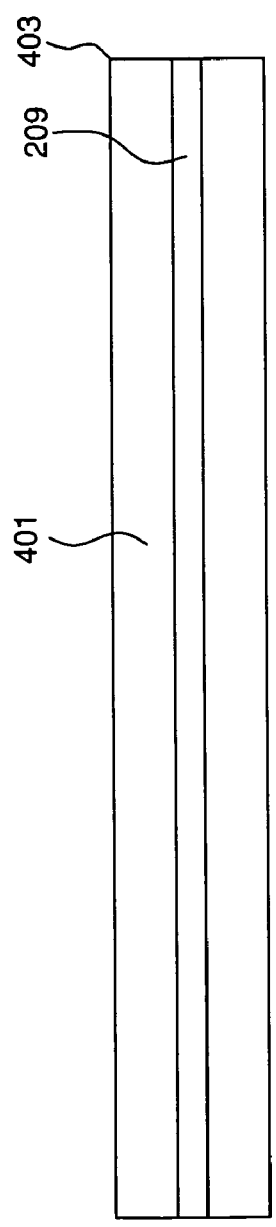
FIG. 4 is a longitudinal cross-sectional view of a guide wire in accordance with an exemplary embodiment of the present invention, wherein the optical fiber is shown residing in the catheter.

In an alternative embodiment, fiber 209 may be contained within an independent structure, such as a guidewire or a separately defined lumen. FIG. 3F and FIG. 4 illustrate fiber 209 encapsulated in a guidewire 401. Fiber 209 is contained within the structure of guidewire 401. Guidewire 401 is typically formed from a rigid or semi-rigid material. Guidewire 401 is inserted into a catheter from one end and used to place the catheter in position in the patient. Fiber 209 resides in guidewire 401 and is used to locate the distal end 403 of guidewire 401. In an exemplary embodiment, guidewire 401 can be formed by coating fiber 209 with a rigid or semi-rigid material to create the guidewire.

Figure 5:
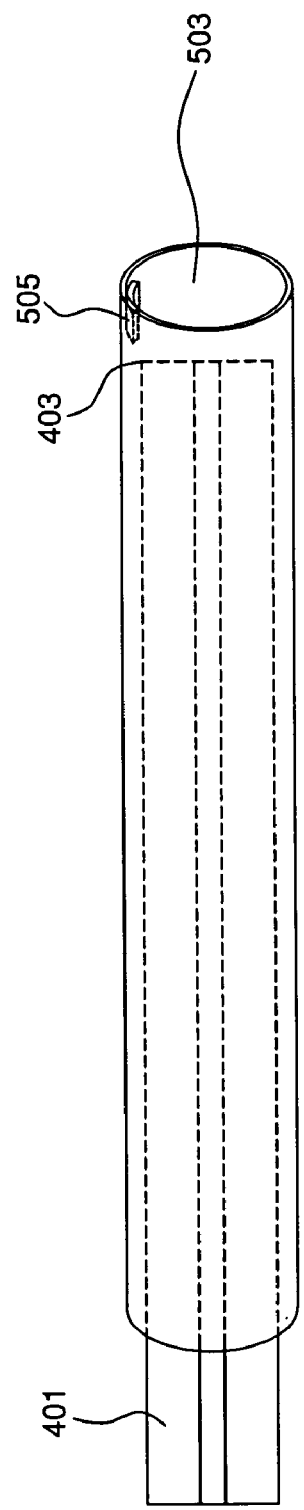
FIG. 5 is a cross-sectional view of a catheter incorporating a guide-wire in accordance with an exemplary embodiment of the present invention.

One concern which arises when fiber 209 is not physically coupled to the catheter is assuring that distal end 403 of guidewire 401 is properly aligned with the distal end of the catheter that is being inserted. Because the aim is to precisely locate the end of the catheter, distal end 403 of guidewire 401 must correspond with the distal end of the catheter. This can be accomplished, for example, by using a pressure or friction fit between guidewire 401 and the inner wall of the lumen in the catheter being placed. Alternatively, a physical stop may be formed to assure proper alignment. Referring to FIG. 5, a catheter 501 is illustrated with guidewire 401 residing in lumen 503. An alignment stop 505 is formed at the end of catheter 501. Guidewire 401 passes through lumen 503 until the distal end 403 of guidewire 401 contacts alignment stop 505.

Referring again to FIG. 2, distal end 103 of catheter 101 is aligned with the light emitting end 210 of fiber 209. Light emitting end 210 of fiber 209 is configured to allow light to be directed in all directions. For example, a teardrop shape or ball shape is formed at the end of fiber 209 to allow the light passing to the light emitting end 210 to be radiated isotropically. One of skill in the art will appreciate various other configurations that are formed at the light emitting end 210 of the fiber 209 to create an isotropic radiation pattern.

Once the signal travels via fiber 209 to emitting end 210 and is isotropically radiated, the radiation passes through the surrounding tissue and exits the patient's body. The radiation is detected by photodetector 111 (as shown in FIG. 1). Various detection devices can be used for detector 111. One embodiment of the invention provides for the operator of the system to use a detection device, such as, but not limited to, near-infrared night vision goggles ("NVG") to directly view the location from which the radiation is being emitted during the placement of the catheter. Additional embodiments utilize photodetectors that capture the radiated signal and provide the signal to a processing center 123 for display on an output device such as display 113 (as shown in FIG. 1).

Referring again to FIG. 1, in an exemplary embodiment, processing center 123 is located on base unit 120. The processing center is coupled to the light source 109, photodetector 111, and a display 113. The processing center processes the data collected by the photodetector 111 and provides for a visual output on the display 113. Signal processing of this nature is well known, and thus is not further described herein.

In addition to locating the position of the catheter 101, an anatomical image of the areas surrounding the emitting end 210 of the fiber 209 can be output on the display. By measuring the strength and direction of the radiated signal received by one or more detection devices, the anatomical structure of the areas through which the signal radiates is determined in either two-dimensions or three-dimensions. For example, light may be detected from many points on the surface of the body. Computational methods are then used to calculate the positions of the source relative to the body surface. The computations use factors, such as the diffusion properties of the light through highly scattering media, the relative positions of the photodetectors on the body surface, and the strengths of the signals at various photodetectors to calculate the precise position of the light source within the body. Using a sufficient number of measurements, the emitting end 210 of the fiber 209 is accurately located and significant information is obtained regarding any internal structures within the body that have different absorption/scattering properties than the surrounding areas. This allows more dense tissues, such as bones, blood vessels, and muscles, to be differentiated from less dense materials, such as air spaces and adipose tissue.

Additionally, the processing center can be used to control the light source to allow for various types of light signals to be coupled into the waveguide. Using the processing center to control the light source permits variation of the light input to the waveguide (e.g., optical fiber). The input signal is thus modulated to correspond with any modulation in the photodetector. For example, in one embodiment the photodetector operates in a manner similar to a camera by taking a snapshot of the emitted radiation at time intervals. The input signal is thus modulated to match the time window of detection. This allows a reduction in the overall power required, thereby providing the advantages of using reduced light intensity as described above. According to this embodiment, the amount/intensity of light emitted from the light source device is controlled so that the amount of light being received is substantially constant. As a result, the picture image is kept at a substantially constant brightness and a higher quality picture image is obtained. By combining this with an automatic gain control, the effect is further enhanced. When the light source is pulsed, causing a flashing of the emitted light, even a static picture image has a high picture quality.

The processing center 123 can further include storage capabilities (e.g., a hard disk drive) for recording the data collected and storing digital images of the pictures displayed on display. This allows for review of the images after the medical procedure is completed, and inclusion in the digital medical record, if desired.

Those skilled in the art will appreciate that other designs of the optical guidance system for catheters in accordance with the invention may be constructed using different light sources and light photodetectors.

Additional objects, advantages and novel features of the invention will be set forth in part in the description and examples which follow, and in part will become apparent to those skilled in the art on examination of the following, or may be learned by practice of the invention. The following examples, however, are understood to be illustrative only and are not to be construed as limiting the scope of the appended claims.

EXAMPLES

Example 1

To demonstrate the effectiveness of the guidance method of the present invention in the alimentary track of a patient, a standard nasogastric feeding tube for an adult human was used. The feeding tube was inserted into the oropharynx of an anesthetized pig. The feeding tube included an optical fiber down the primary lumen of the tube. The tip of the fiber was within 0.5 cm of the tip of the feeding tube. Room lighting was minimized. Using night vision goggles and a camera/monitor system (Gen III intensified CCD camera ITT Industries Night Vision, San Diego, Calif.) insertion of the catheter could be followed very easily from the mouth to the stomach. The point of light emitted from the end of the optical fiber could easily be seen on the monitor as the feeding tube was advanced and placed.

The system was further tested on a human subject, a 210 lb man. An optical fiber (200 micron diameter core) was inserted into the nasogastric tube until the optical fiber was within a half centimeter of the tip of the distal end of tube 101 and the optical fiber was fixed (taped) in place at the external port of the tube. The external (proximal) end of the optical fiber terminated with a SMA fiber optic connector, which was then coupled to an approximately 20 mW CW LD, producing a light wavelength of 780 nm. There are many different types of connectors in use with fiber optic systems of the type used in this optically-guided catheter system. The SMA connector, which was first developed before the invention of single-mode fiber, was the most popular type of connector until recently, when it was replaced in popularity by the ST multimodal connector. Additional suitable connectors will continue to be developed.

Images were recorded showing the controlled positioning/movement of the nasogastric tube. The images were viewed and recorded at different stages of the insertion using approximately 0.1 sec exposures, by a Gen III intensified CCD camera (ITT Industries Night Vision, San Diego, Calif. 92126) through a 696 nm long pass glass filter, 3 mm in thickness (Schott Glass, Schott North America, Elmsford, N.Y.).

The images were visible at each stage of insertion from the time just after the tip of the optically-guided nasogastric tube entered the nasal passage until it had passed through the pyloric sphincter and proceeded posteriorly in the small intestine. The room light was adjusted to enhance viewing capability, such that there was a weak image of the person to permit accurate determination of the position of the tip of the tube.

A critical stage of the insertion was noted when the tip of the light-guided nasogastric tube passed into the chest cavity of the patient, after which the emitted light could be seen, but only very weakly, as the light emitted from the distal end of the tube passed through the chest. However, as the lighted tip emerged from the chest into the stomach, the signal became very bright and was easily tracked as it passed across the abdomen within the stomach. As the lighted tip passed from the stomach into the small intestine, it passed through the pyloric sphincter and crossed midline into the duodenum. The pyloric sphincter is a narrow circular muscle at the junction of the stomach and the small intestine. As expected, the dense muscle of the sphincter absorbed substantially more light than the stomach or small intestine on either side. As a result, when the light source was half-way through the pyloric sphincter the light reaching the surface of the abdomen took on a dual lobe appearance transdermally and was clearly visible on the monitor. This resulted from the shadow of the sphincter muscle bisecting the lighted region. Thus, the shadow of the sphincter muscle precisely indicated when the tip of the feeding tube passed from the stomach into the small intestine, easily and reliably permitting precise placement of the tip of the optically-guided nasogastric tube. This placement was further aided by observing the tip of the feeding tube pass the midline point and continuing to the right side of the body, indicating that it was post-pyloric.

Example 2

While demonstrating the effectiveness of the guidance method of the present invention for positioning intravascular catheters, an additional useful feature was noted. When an optical fiber and near infrared light LD system was added, as described above, to a peripherally inserted central venous catheter (PICC) line and placed in accordance with standard PICC practice in a vein leading to the heart, it was observed that as the lighted tip of the catheter neared the heart, the light became modulated by the movement of the beating heart. Moreover, as the lighted tip entered the heart, the light (signal) was greatly attenuated.

The heart consists of heavy, dense muscle, and the muscle tissue strongly attenuates the near infrared laser light, as compared to the surrounding environment. This is because the heart is suspended in what is mostly open space (lung, chest cavity), which easily transmits near-infrared light. Light emitted from the end of the catheter travels in all directions (360° radii) within the chest cavity, however the light is absorbed when it hits the heart. Accordingly, as the lighted catheter tip approaches the heart, the movement of the heart causes modulation of the light transmitted to the surface of the body, wherein the modulation intensity increases as the tip gets closer to the outer edge of the heart. Thus, the intensity of the light pulsates, synchronously with the heart beat. However, as the lighted tip actually enters the heart and is surrounded by heart muscle, the light intensity decreases dramatically and the modulation effectively ceases due to the low level of measured light. These observations were confirmed with x-rays.

By this method, an operator literally "sees" via the detector that the catheter is in the correct vessel, that it is nearing the heart, and then that it has been advanced too far and has entered the heart by observing the modulation of the emitted light. Because the emitted light is clearly detected, the operator can easily identify the tip of the optically-guided PICC line as it enters the vessels near the heart. The visible catheter tip can then be precisely advanced until it pulsates, signaling optimal position. If the catheter is advanced into the heart, the light is occluded and the catheter tip will no longer be visible. In this situation, the catheter is withdrawn to a pre-selected distance from the heart such that the emitted light is again visible and appears to be pulsating.

In the embodiment in which the waveguide is fixed to the catheter and not removable (in contrast with the stylet or guidewire application), the position of an optically-guided catheter can be checked at any time by simply reconnecting the catheter to the imaging system, turning on the laser light, and observing the modulation of the light intensity caused by the movement of the heart. There are several advantages to this, including that radiation and x-ray images are not required. Also, it requires neither moving the patient to an x-ray suite, nor moving bulky portable x-ray equipment to the patient's room. Consequently, the present technology and method of using the emitted light from an optically-guided PICC permits easy determination of the proximity of the catheter tip to the heart and will greatly enhance the accuracy and precise placement of central venous catheters, including PICC lines.

Example 3

In another example of the guidance system, a light-guided epidural catheter was inserted into the lower lumbar region of a large pig. Pigs are representative of humans for this invention, as shown in Example 1. The epidural space was accessed in the standard manner by palpation of spinous processes, insertion of an 18 gauge Toughy needle to the depth of the epidural space using the air/fluid technique and a glass syringe. A standard epidural catheter was used, having an optical fiber within its lumen, threaded to the distal tip of the catheter and secured to the catheter (tape was used in this example, but any of the above disclosed methods for securing and/or sealing the optical fiber to the catheter would be effective).

In ambient light, the epidural catheter was advanced in the subject and the transdermally emitted point of light was captured and followed by the imaging system as it moved from the lower lumbar region to the thoracic region. Using a filtered camera/monitor system (e.g., an Astrovid StellaCam EX Video Camera filtered with a Schott AG 745 nm LongPass filter) the location of the lighted tip of the catheter was easily identified through the entire process.

The catheter was removed and the needle was advanced into the intrathecal space. The light-guided catheter was then reinserted. Again the catheter was observed, by means of the light guide at the tip of the catheter, as it traveled the entire distance in the intrathecal space, as it had in the epidural space. The light output was only slightly diminished with the increased depth of the lighted tip of the catheter in the body of the subject, but the effectiveness of the light-guided system for the precise placement of the catheter in the subject was not affected.

Each and every patent, patent application and publication that is cited in the foregoing specification is herein incorporated by reference in its entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

What is claimed is:

1. A method of precisely placing a light-emitting point on an optically-guided catheter within a patient, the method comprising:
   inserting the optically-guided catheter into a patient vessel of the patient;
   emitting light from a light-emitting point on the catheter within the patient;
   moving the light-emitting point in proximity to the patient's heart;
   externally detecting light emitted from the light-emitting point on the catheter within the patient, wherein the light is transdermally projected from within the patient;
   observing changes in pattern of emitted light as the light-emitting point approaches the patient's heart;

determining location of the light-emitting point within the patient, based upon the externally detected light; and determining placement of the catheter within the patient, based upon location of the light-emitting point;

wherein in proximity to the heart, the emitted light fluctuates in intensity synchronously with heart beats, thereby indicating the location of the distal end of the optically-guided catheter within the patient vessel in relation to the patient's heart.

2. The method according to claim 1, wherein the detecting is performed using a detection device.

3. The method according to claim 2, wherein the detecting comprises photodetecting.

4. The method according to claim 2, wherein the detecting further comprises filtering the emitted light by a filter coupled to the detection device.

5. The method according to claim 4, wherein the filter is a narrow band interference filter.

6. The method according to claim 2, wherein the detection device comprises night vision goggles.

7. The method according to claim 1, wherein emitting the light utilizes a waveguide extending from a light source to the light-emitting point.

8. The method according to claim 7, wherein the light source is an LED or LD.

9. The method according to claim 7, wherein the light has a wavelength in the range of 620 nm to 1500 nm.

10. The method according to claim 7, wherein the waveguide comprises an optical fiber.

11. The method according to claim 1, wherein emitting the light further comprises coupling a light source at the light emitting point on the catheter, and generating the light therefrom.

12. The method according to claim 11, wherein the light source is an LED or LD.

13. The method according to claim 1, wherein the optically-guided catheter is a peripherally inserted central catheter, inserted into a blood vessel leading to the heart of the patient, and wherein the emitted-light is emitted from the distal end of the peripherally inserted central catheter.

14. The method according to claim 13, wherein the method further comprises: observing a marked occlusion of emitted light from the distal end of the peripherally inserted central catheter when the peripherally inserted central catheter end is advanced within the vessel and enters into the patient's heart; observing return of the emitted light to its non-occluded state when the distal end of the peripherally inserted central catheter is withdrawn into the vessel from the heart muscle; and based upon observed qualitative changes in the emitted light, rapidly confirming placement of, or changing placement of, the optically-guided peripherally inserted central catheter in the patient.

* * * * *